United States Patent [19]

Baer et al.

[11] Patent Number: 5,049,488
[45] Date of Patent: Sep. 17, 1991

[54] METHOD AND NUCLEIC ACID FOR THE PREPARATION OF LECITHIN:CHOLESTEROL ACYLTRANSFERASE

[75] Inventors: Bradford W. Baer, Menlo Park; Dennis T. Drayna, San Francisco; Richard M. Lawn, San Francisco; John W. McLean, San Francisco, all of Calif.

[73] Assignee: Genentech, Inc., South San Francisco, Calif.

[21] Appl. No.: 796,473

[22] Filed: Nov. 8, 1985

[51] Int. Cl.⁵ .............................................. C12Q 1/68
[52] U.S. Cl. .................................... 435/6; 435/803; 435/172.3; 436/501; 536/27; 530/397; 935/78
[58] Field of Search .................... 435/6, 803, 172.3; 436/501; 536/27; 530/397; 935/78

[56] References Cited

U.S. PATENT DOCUMENTS 4,358,535  11/1982  Falkow et al. ................... 435/35 X
4,491,631   1/1985  Imamura et al. ................. 435/11 X
4,499,184   2/1985  Goodhue .......................... 435/11

OTHER PUBLICATIONS

Wood, W. I. et al., Nature 312, Nov. 1984, pp. 330-337.
Boguski, M. S. et al., Proc. Natl. Acad. Sci. U.S.A., 82, Feb. 1985, pp. 992-996.
McLean, J. W. et al., J. Biol. Chem. 259 1984, pp. 6498-6504.
McLean, J. et al., Nucleic Acids Res 14, 1986, pp. 9397-9406.
Chem. Abst. 90 No. 15, issued 4/9/79, p. 447 #119261j, Dobiasova, M. et al., "Lecithin:Cholesterol Acyltransferase . . . Heart Disease".

Primary Examiner—Robert A. Wax
Assistant Examiner—Ardin H. Marschel
Attorney, Agent, or Firm—Max D. Hensley; Robert H. Benson

[57] ABSTRACT

Nucleic acid encoding lecithin:cholesterol acyltransferase is ligated into expression vectors and used to transform host cells for the synthesis of lecithin:cholesterol acyltransferase in recombinant cell culture. Lecithin:cholesterol acyltransferase amino acid sequence variants are described for enhancing the properties of lecithin:cholesterol acyltransferase. Lecithin:cholesterol acyltransferase and its variants are employed in the therapy of conditions characterized by hypercholesterolemia and for the mobilization of cholesterol in vivo.

4 Claims, 5 Drawing Sheets

Fig. 2a.

```
                    -21
          Met Gly Pro Pro Gly Ser Pro Trp Gln Trp Val Thr Leu Leu Gly Leu Leu Pro Pro Ala Ala Pro
  1       ATG GGG CCG CCC GGC TCC CCA TGG CAG TGG GTG ACG CTG CTC GGG CTG CTC CCT CCT GCC GCC CCC
CCAGGGCTGGA                                                              -11                    -1

1                                               21
          Phe Trp Leu Leu Asn Val Leu Phe Pro Pro His Thr Thr Pro Lys Ala Glu Leu Ser Asn Trp Ile Leu
  84      TTC TGG CTC CTC AAT GTG CTC TTC CCC CCG CAC ACC ACA CCC AAG GCT GAG CTC AGT AAC TGG ATC CTC 31                                              51
          Val Pro Gly Cys Leu Gly Asn Gln Leu Asp Leu Asp Lys Leu Asp Lys Pro Asp Val Val Tyr Arg Lys Thr
  165     GTG CCC GGC TGC CTG GGG AAT CAG CTA GAC CTA GAA GCC CTA AAA CCA GAT GTG GTG TAC CGC AAG ACA 61                                              81
          Glu Asp Phe Phe Thr Ile Trp Leu Asp Leu Asn Met Phe Leu Pro Leu Gly Val Asp Cys Trp Met Cys Arg Val
  246     GAG GAC TTC TTC ACC ATC TGG CTG GAT CTC AAC ATG TTC CTA CCC CTT GGG GTA GAC TGC TGG ATG TGC CGC GTT

Val Tyr Asn Arg Ser Ser Gly Leu Val Ser Asn Ala Pro Gly Tyr Leu His Thr Leu Arg Val Gln Asn Leu Pro Gly Phe Gly Lys Thr Tyr Ser
  327     GTC TAC AAC CGG AGC TCT GGG CTC GTG TCC AAC GCC CCT GGT TAC CTG CAC ACA CTG CGC GTC CAG AAC CTG CCT GGG TTT GGC AAG ACC TAC TCT
                                                           101
                               111                                              131
          Val Glu Tyr Leu Asp Ser Lys Leu Ala Gly Tyr Asp Trp Arg Leu Glu Pro Gly Gln Gln Glu Glu Pro Lys Leu Val Asn Asn Gly Tyr Val Arg
  408     GTG GAG TAC CTG GAC AGC AAG CTG GCA GGG TAC GAC TGG CGG CTG GAG CCC GGC CAG CAG GAG GAG CCC AAG CTG GTC AAC AAT GGC TAC GTG CGG
                                                           121
                               141                                              161
          Asp Thr Val Arg Ala Ala Ala Pro Tyr Arg Leu Glu Pro Gly Gln Gln Glu Glu Pro Lys Leu Lys Leu Ala Gly
  489     GAC ACT GTG CGC GCC GCC GCT TAT CGG CTG GAG CCC GGC CAG CAG GAG GAG CCC AAG CTC GCA GGG
                                                           151
                   171                                              181
          Leu Val Glu Glu Met His Ala Ala Tyr Gly Lys Pro Val Phe Leu | Ile Gly His Ser Leu Gly | Cys Leu His Leu Leu Tyr
  570     CTG GTG GAG GAG ATG CAC GCT GCT TAT GGG AAG CCT GTC TTC CTC | ATT GGC CAC AGC CTC GGC | TGT CTA CAC TTG CTC TAT
```

```
          191                                        201
      Phe Leu Arg Gln Pro Gln Ala Trp Lys Asp Arg Phe Ile Asp Gly Phe Ile Ser Leu Gly Ala Pro Trp Gly Gly Ser
 651  TTC CTG CGC CAG CCC CAG GCC TGG AAG GAC CGC TTT ATT GAT GGC TTC ATC TCT CTT GGG GCT CCC TGG GGT GGC TCC
          221                                        231                                        241
      Ile Lys Pro Met Leu Val Leu Ala Ser Gly Asp Asn Gln Gly Ile Pro Ile Met Ser Ser Ile Lys Leu Lys Glu Gln
 732  ATC AAG CCC ATG CTG GTC TTG GCC TCA GGT GAC AAC CAG GGC ATC CCC ATC ATG TCC AGC ATC AAG CTG AAA GAG CAG
          251                                        261
      Arg Ile Thr Thr Thr Ser Pro Met Phe Trp Pro Ser Arg Met Ala Trp Pro Glu Asp His Val Phe Ile Ser Thr Pro Ser
 813  CGC ATA ACC ACC ACC TCC CCC ATG TTT CCC TCT CGC ATG GCG TGG CCT GAG GAC CAC GTG TTC ATT TCC ACA CCC AGC
          271                                        281                                        291
      Phe Asn Tyr Thr Gly Arg Asp Phe Gln Arg Phe Ala Asp Leu His Phe Glu Gly Trp Tyr Met Trp Leu Gln Ser
 894  TTC AAC TAC ACA GGC CGT GAC TTC CAA CGC TTC GCA GAC CTG CAC TTT GAG GAA GGC TGG TAC ATG TGG CTG CAG TCA
          301                                        311                                        321
      Arg Asp Leu Leu Ala Gly Leu Ala Pro Gly Val Glu Val Tyr Cys Leu Tyr Gly Val Gly Leu Pro Pro Arg Thr
 975  CGT GAC CTC CTG GCA GGA CTC GCA CCT GGT GTG GAA GTA TAC TGT CTT TAC GGC GTG CTG CCC ACG CCC CGC ACC
          331                                        341                                        351
      Tyr Ile Tyr Asp His Gly Phe Pro Tyr Thr Asp Pro Val Gly Val Leu Tyr Glu Asp Gly Asp Thr Val Ala Thr Arg
1056  TAC ATC TAC GAC CAC GGC TTC CCC TAC ACG GAC CCT GTG GGT GTG CTC TAT GAG GAT GGT GAC ACG GCG ACC CGC
          361                                        371
      Ser Thr Glu Leu Cys Gly Leu Trp Gln Gly Arg Gln Pro Val His Leu Pro Leu Leu His Gly Ile Gln His Leu
1137  AGC ACC GAG CTC TGT GGC CTG TGG CAG GGC CGC CAG CCT GTG CAC CTG CCC CTG CTG CAC GGG ATA CAG CAT CTC
          381                                        391                                        401
      Asn Met Val Phe Ser Asn Leu Thr Leu Glu His Ile Asn Ala Ile Leu Leu Gly Ala Tyr Arg Gln Gly Pro Pro Ala Ser
1218  AAC ATG GTC TTC AGC AAC CTG ACC CTG GAG CAC ATC AAT GCC ATC CTG CTG GGT GCC TAC CGC CAG GGT CCC CCT GCA TCC
          411
      Pro Thr Ala Ser Pro Glu Pro Pro Pro Glu End
1299  CCG ACT GCC AGC CCA GAG CCC CCG CCT GAA TAAAGACCTTCCTTTGCTACCGTA$_n$
```

Fig. 2b.

5' flanking and untranslated

```
  1 TGAGGCCTGA CTTTTTCAAT AAAACATTGT GTAGTTCTGG GCCTCCTGCT GCCCCGGCTC TGTTTCCCT GGGGCCAAGA GAAGAAGGCG GAACTGAACC
101 CAGGCCCAGA GCCGGCTCCC TGAGGCTGTG CCCCTTTCCG GCAATCTCTG GCCACAACCC CCACTGGCCA GGCCGTCCCT CCCACTGGCC CTAGGGCCCC
                                                                                                        Met Gly Pro Pro Gly Ser Pro Trp
                                                                                                        ATG GGG CCG CCC GGC TCC CCA TGG
201 TCCCACTCCC ACACCAGATA AGGACAGCCC AGTGCCGCTT TCTCTGGCAG TAGGCACCAG GGCTGGA
```

3' flanking and untranslated

```
      411
      Thr Ala Ser Pro Glu Pro Pro Pro Pro Glu End
1302  ACT GCC AGC CCA GAG CCC CCG CCT CCT GAA TAA    AGACCTTC CTTTGCTACC GTAAGCCCTG ATGGCTATGT TTCAGGTTGA AGGGAGGCAC
1394  TAGAGTCCCA CACTAGGTTT CACTCCTCAC CAGCCACAGG CTCAGTGCTG TGTGCAGTGA GGCAAGATGG GCTCTGCTGA GGCCTGGGAC TGAGCT
```

METHOD AND NUCLEIC ACID FOR THE PREPARATION OF LECITHIN:CHOLESTEROL ACYLTRANSFERASE

BACKGROUND

This invention relates to the preparation of lecithin:cholesterol acyltransferase. In particular, this invention is concerned with the expression of lecithin:cholesterol acyltransferase in recombinant host cell culture.

Cholesterol of peripheral origin is transported through the plasma for catabolism in the liver. The sequence of reactions involved in this pathway (reverse cholesterol transport) is believed to be important in peripheral cholesterol homeostatis (1). A key component in the process of transport and metabolism of cholesterol in plasma is its esterification by lecithin:cholesterol acyltransferase. This enzyme, a glycoprotein of apparent molecular weight ~63,000 (2,3), is secreted from the liver into the plasma compartment (4,5). Under physiological conditions, lecithin:cholesterol acyltransferase catalyzes the transfer of acyl groups from the sn2 position of lecithin to the 3-OH of free cholesterol. Apolipoprotein A-I (apoA-I), the major protein of plasma high density lipoprotein (HDL) is a potent activator of lecithin:cholesterol acyltransferase activity (6). The conversion of diffusible cholesterol to its insoluble ester form in plasma is important in maintaining a concentration gradient between cell membranes and plasma. When lecithin:cholesterol acyltransferase activity is inhibited in vitro or in vivo, or is genetically defective, cholesterol is no longer transported to plasma, and accumulates in the tissues (7-9). While the lecithin:cholesterol acyltransferase protein has been purified to homogeneity by several laboratories, little is known of its structure of mechanism of action. Furthermore, purification from natural sources is expensive and there is a risk of contamination in the final product from adventitious viruses and the like. In addition, the activity of natural lecithin:cholesterol acyltransferase, i.e., lecithin:cholesterol acyltransferase having an amino acid sequence identical to that of lecithin:cholesterol acyltransferase present in a given animal species (or its naturally-occurring alleles), is not readily modified. Accordingly, it is an object herein to provide a method for the economical preparation of lecithin:cholesterol acyltransferase free of infective contamination and which is sufficiently flexible to enable the preparation of lecithin:cholesterol acyltransferase amino acid sequence variants having properties that differ from those of natural lecithin:cholesterol acyltransferase.

SUMMARY

The above objects are achieved by a method comprising (a) constructing a vector comprising nucleic acid encoding lecithin:cholesterol acyltransferase; (b) transforming a host cell culture with the vector of step a); (c) culturing the transformant of step b) to accumulate lecithin:cholesterol acyltransferase in the culture; and (d) recovering the lecithin:cholesterol acyltransferase from the culture.

We have constructed and sequenced full-length lecithin:cholesterol acyltransferase cDNA clones, provided the complete translated amino acid sequence of the mature lecithin:cholesterol acyltransferase protein and its leader prepeptide, and provided methods for its expression in recombinant cell culture. Surprisingly, this enzyme has been expressed in recombinant cell culture in an enzymatically active form without evident host cell toxicity, notwithstanding the critical role that cholesterol and other lipids play in maintaining cell membrane integrity.

Methods are provided for the preparation of lecithin:cholesterol acyltransferase amino acid sequence variants that exhibit improved properties such as enhanced oxidative stability, reduced susceptibility to proteolytic hydrolysis in cell culture or in in vivo therapy and modification of lecithin:cholesterol acyltransferase apolipoprotein and cofactor binding characteristics.

Lecithin:cholesterol acyltransferase-associated DNA identified herein is used in hybridization assays for the identification of heart disease-linked restriction enzyme polymorphisms.

Such assays are useful in screening for prenatal congenital Lecithin:cholesterol acyltransferase deficiency and predisposition to heart disease in adults.

Lecithin:cholesterol acyltransferase is administered in therapeutically effective doses to patients having lecithin:cholesterol acyltransferase deficiency, e.g. those having congenital deficiencies, endstage renal disease or hepatitis, in physiologically acceptable carriers. Plasma cholesterol levels are reduced upon the lecithin:cholesterol acyltransferase mediated mobilization of plasma cholesterol into high density lipoproteins and its removal from the bloodstream. Lecithin:cholesterol acyltransfersase also is believed to be as useful in aiding in the mobilization of cholesterol from atherosclerotic plaques as it is in mobilizing cholesterol from other tissues.

BRIEF DESCRIPTION OF THE DRAWINGS

FIG. 2a illustrates the amino acid and nucleotide sequence for a cDNA encoding natural human lecithin:cholesterol acyltransferase cDNA. The nucleotides (left of each row) are numbered from the 5' terminus of cDNA clone pL12. The complete predicted amino acid sequence of lecithin:cholesterol acyltransferase is shown above the DNA sequence. Negative amino acid numbers (above residues) refer to the presumed leader prepeptide, while positive numbers refer to the mature protein. The four predicted N-linked glycosylation sites are overlined, and the six residue stretch (surrounded by hydrophilic regions) which is identical to the interfacial binding site of porcine pancreatic lipase, is boxed in.

Double underlines indicate the conserved polyadenylation signal hexanucleotide. Poly(A) tails of varying length occur at the same location in four cDNA clones. The single underlines show the amino acid sequences obtained by N-terminal sequencing as well as analysis of peptides obtained upon trypsin hydrolysis.

FIG. 2b depicts the genomic sequence obtained from bacteriophage lambda clones which overlap the 5' and 3' ends of the cDNA, respectively. 5'-flanking nucleotides are arbitrarily numbered from the 5' end of the available sequence. The amino-terminal lecithin:cholesterol acyltransferase protein sequence is numbered as in FIG. 2a. Stop codons in all three reading frames are underlined. The first in-frame upstream stop codon is the TGA of nucleotides 121–124. The 3'-flanking nucleotides and carboxy-terminal peptides are numbered as in FIG. 2a. The polyadenylation signal hexanucleotide is double underlined and the site of poly(A) tail addition is single underlined.

Figure 3:
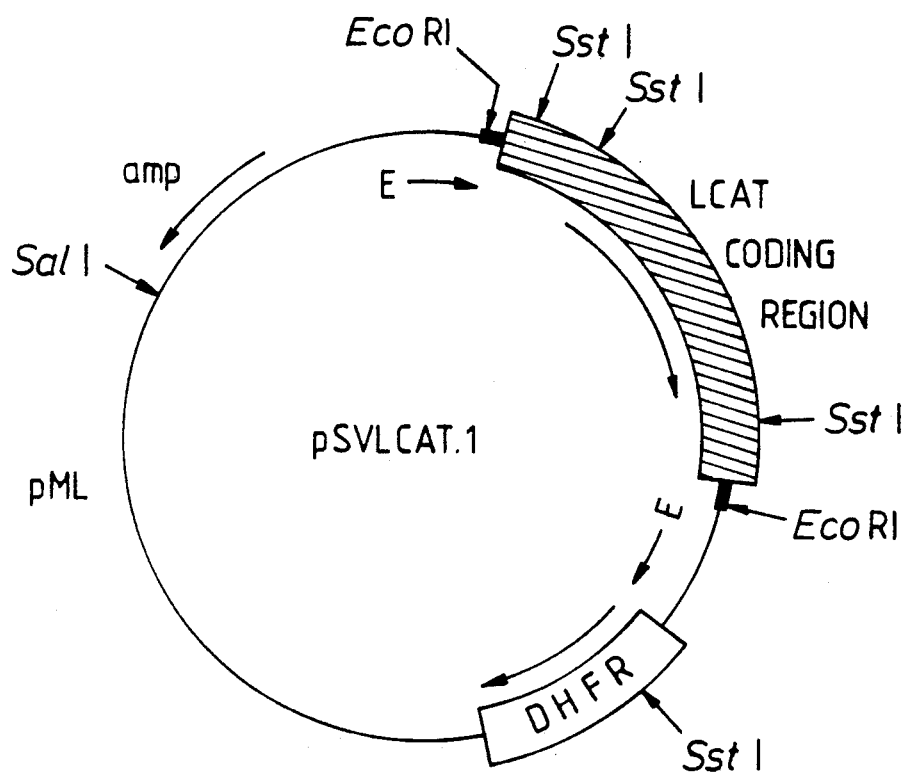

FIG. 3 shows the lecithin:cholesterol acyltransferase expression vector pSVLCAT.1. E designates the SV40 early promoter. The directions of transcription are designated by arrows.

DETAILED DESCRIPTION

Lecithin:cholesterol acyltransferase is defined for the purposes herein as a protein having the amino acid sequence set forth in FIG. 2a and its amino acid sequence variants, including naturally occurring alleles and variants having predetermined deletions, insertions or substitutions of one or more residues, which are either enzymatically active in esterifying cholesterol or which are enzymatically inactive but remain immunologically cross-reactive with an antibody capable of binding enzymatically active lecithin:cholesterol acyltransferase.

Immunologically cross-reactive lecithin:cholesterol acyltransferase variants are capable of competitively inhibiting the binding of a enzymatically-active lecithin:cholesterol acyltransferase with polyclonal antisera raised against enzymatically-active lecithin:cholesterol acyltransferase. Such antisera are prepared in conventional fashion by injecting goats, birds, rabbits or other species S.C. with lecithin:cholesterol acyltransferase in complete Freund's adjuvant, followed by booster intraperitoneal or S.C. injections incomplete Freunds.

Lecithin:cholesterol acyltransferase variants that are not enzymatically-active but which are capable of cross-reacting with antisera to enzymatically-active lecithin:cholesterol acyltransferase are useful (a) as a reagent in diagnostic assays for lecithin:cholesterol acyltransferase, or antibodies to lecithin:cholesterol acyltransferase, (b) when insolubilized in accord with known methods, as an agent for purifying anti-lecithin:cholesterol acyltransferase antibodies from antisera or binding proteins from plasma, and (c) as an immunogen for raising antibodies to enzymatically-active lecithin:cholesterol acyltransferase.

The amino acid sequence of FIG. 2a is that of prelecithin:cholesterol acyltransferase. While prelecithin:cholesterol acyltransferase is synthesized, for example, in prokaryotes transformed with DNA encoding prelecithin:cholesterol acyltransferase which do not process and secrete mature lecithin:cholesterol acyltransferase from the mammalian preprotein, it is preferable to transform host cells capable of undertaking such processing so as to obtain mature lecithin:cholesterol acyltransferase in the culture medium or periplasm of the host cell. Typically, higher eukaryotic host cells such as mammalian cells are capable of processing prelecithin:cholesterol acyltransferase and secreting mature lecithin:cholesterol acyltransferase upon transformation with DNA encoding prelecithin:cholesterol acyltransferase.

Alternatively, secreted mature lecithin:cholesterol acyltransferase is obtained 5' ligating DNA encoding mature lecithin:cholesterol acyltransferase to the 3' end of DNA encoding a signal sequence homologous to the host and this construction used to transform host cells. The term "homologous" means that the sequence in question is that of a protein or polypeptide normally present within the host cell. In this case, the host cell will process the expressed fusion by proteolytically cleaving the peptide bond between the signal sequence and the $Phe_1$ of lecithin:cholesterol acyltransferase, and thereafter secrete the mature lecithin:cholesterol acyltransferase into the host cell periplasm or into the medium, depending upon the host cell in question. For example, in constructing a proacryotic expression vector the human lecithin:cholesterol acyltransferase secretory leader is replaced by the bacterial alkaline phosphatase or heat stable enterotoxin II leaders, and for yeast the lecithin:cholesterol acyltransferase leader is replaced by the yeast invertase, alpha factor or acid phosphatase leaders. However, human the lecithin:cholesterol acyltransferase secretory leader is recognized by heterologous higher eukaryotic cells. Gram negative organisms transformed with a homologous signal-lecithin:cholesterol acyltransferase fusion will secrete mature lecithin:cholesterol acyltransferase into the cell periplasm, whereas yeast or *bacillus sp.* will secrete mature lecithin:cholesterol acyltransferase into the culture medium.

Amino acid sequence variants are lecithin:cholesterol acyltransferase species in which at least one amino acid residue is deleted, inserted or substituted by another residue. Such variants are prepared in order to modify the characteristics of the lecithin:cholesterol acyltransferase enzyme to enhance its therapeutic efficacy or facilitate its preparation in recombinant cell culture. Typical variants will be engineered, for example, to resist proteolytic hydrolysis that may occur in some recombinant cell cultures or in the circulation of patients to whom lecithin:cholesterol acyltransferase is administered by rendering proteolysis sites no longer susceptible to proteolytic attack. This is suitably accomplished by deleting or substituting argininyl and lysinyl residues by other residues, or by inserting prolyl residues after such argininyl or lysinyl residues.

Other variants will be glycosylation resistant (by deletion or substitution of asparaginyl residues in Asn X Thr glycosylation sites) or glycosylated at novel predetermined sites (by insertions or substitutions to create an Asn X Thr site). Variants also are produced which modify the enzyme catalytic activity, e.g. that broaden its substrate specificity or increase its turnover number, which entail deletion of oxidatively labile residues in the enzyme and which vary in their ability to bind to apolipoprotein D and other proteins, including cell surface receptors, with which lecithin:cholesterol acyltransferase may interact.

Amino acid sequence variants of prelecithin:cholesterol acyltransferase or mature lecithin:cholesterol acyltransferase fall into several classes: deletions, insertions or substitutions. Insertions include amino and/or carboxyl terminal fusions as well as intrasequence insertions of single residues or polypeptides. Fusions include hybrids of mature lecithin:cholesterol acyltransferase with polypeptides that are homologous with lecithin:cholesterol acyltransferase including, in the case of human lecithin:cholesterol acyltransferase, secretory leaders from other secreted human proteins, polypeptides that are homologous with the host cell, e.g., secretory leaders of host cell proteins, and polypeptides that are heterologous to both the host cell as well as the species from which the lecithin:cholesterol acyltransferase was derived. Preferred fusions with the scope of this invention are amino terminal fusions with either prokaryotic peptides or signal peptides of prokaryotic, yeast, viral or host cell signal sequences. It is not essential that the signal sequence be devoid of any residual mature sequence from the protein whose secretion it ordinarily directs, but this is preferable in order to avoid the secretion of a lecithin:cholesterol acyltransferase fusion.

Other insertions are introduced within the mature coding sequence of lecithin:cholesterol acyltransferase. These, however, ordinarily will be smaller insertions than amino or carboxyl terminal fusions, on the order of 1 to 4 residues. Generally, they should be introduced in pairs in order to minimize the introduction of perturbations into the lecithin:cholesterol acyltransferase molecule. A representative example is [$Arg_{362} \rightarrow Arg_{362}$-$ProGln_{363}$]lecithin:cholesterol acyltransferase, a variant selected for its resistance to trypsin hydrolysis at the $Arg_{362}$ residue. An additional insertional variant is [$Pro_{174}Val_{175} \rightarrow Pro_{174}Val$ $ValVal_{175}$]lecithin:cholesterol acyltransferase. Unless otherwise stated, the specific lecithin:cholesterol acyltransferase variations described herein are variations in the mature lecithin:cholesterol acyltransferase sequence; they are not prelecithin:cholesterol acyltransferase variants.

Deletions are characterized by the removal of one or more amino acid residues from the lecithin:cholesterol acyltransferase sequence. They are preferably introduced in pairs for the same reason as with insertions. For example, $Gly_{172}Lys_{173}$ is deleted in order to destroy a trypsin hydrolysis site. Other lecithin:cholesterol acyltransferase deletional variants are [$Glu_{411}Pro_{412} \rightarrow \Delta$]lecithin:cholesterol acyltransferase and [$Asn_{272}Tyr_{273} \rightarrow \Delta$]lecithin:cholesterol acyltransferase. Typically, no more than about from 2 to 6 residues are deleted at any one site within the lecithin:cholesterol acyltransferase molecule, although deletion of residues $-23$ to $-1$ inclusive will be undertaken to obtain met-lecithin:cholesterol acyltransferase, a variant adopted for intracellular direct expression of met-mature lecithin:cholesterol acyltransferase.

Substitution variants are characterized by the removal of a target residue and its replacement by another amino acid. Compared to deletional or insertional variants, larger numbers of substitutions can be made, particularly when residues having similar steric bulk and charge or hydrophobicity are substituted for the target residue. In general, substitutions permit fine modifications in lecithin:cholesterol acyltransferase activity and characteristics, more so than ordinarily is feasible with deletions or insertions. Exemplary substitutions include [$Phe_{176} \rightarrow Tyr_{176}$]lecithin:cholesterol acyltransferase; [$Val_{175} \rightarrow Thr_{175}$]lecithin:cholesterol acyltransferase; [$Lys_{173} \rightarrow Glu_{173}$]lecithin:cholesterol acyltransferase; [$Lys_{173} \rightarrow His_{173}$]lecithin:cholesterol acyltransferase; [$Cys_{356} \rightarrow Ser_{356}$]lecithin:cholesterol acyltransferase; [$Lys_{15} \rightarrow Asn_{15}$]lecithin:cholesterol acyltransferase; [$Arg_{158} \rightarrow Trp_{158}$]lecithin:cholesterol acyltransferase; [$Arg_{256} \rightarrow Trp_{256}$]lecithin:cholesterol acyltransferase; [$Arg_{323} \rightarrow His_{323}$]lecithin:cholesterol acyltransferase; [$Arg_{256} \rightarrow Trp_{256}$]lecithin:cholesterol acyltransferase; [$Arg_{147} \rightarrow Trp_{147}$]lecithin:cholesterol acyltransferase; [$Arg_{140} \rightarrow Asn_{140}$]lecithin:cholesterol acyltransferase; [$Lys_{105} \rightarrow His_{105}$]lecithin:cholesterol acyltransferase; [$Lys_{116} \rightarrow His_{116}$]lecithin:cholesterol acyltransferase; [$Lys_{101} \rightarrow Gln_{101}$; $Lys_{116} \rightarrow Asn_{116}$; $Arg_{140} \rightarrow Asn_{140}$; $Arg_{147} \rightarrow His_{147}$; $Arg_{158} \rightarrow Asn_{158}$]lecithin:cholesterol acyltransferase; [$Ser_{181} \rightarrow Thr_{181}$]lecithin:cholesterol acyltransferase; and [$His_{180} \rightarrow Asn_{180}$]lecithin:cholesterol acyltransferase.

Combinations of deletions, insertions and/or substitutions of amino acid residues also are within the scope of this invention. For example, [$Thr_{22} \rightarrow \Delta$; $Phe_{67} \rightarrow Thr_{67}$]lecithin:cholesterol acyltransferase or [$Leu_{183} \rightarrow Val_{183}$; $Leu_{185}His_{186} \rightarrow Leu_{185}ValValHis_{18}$]lecithin:cholesterol acyltransferase.

Amino acid sequence variants are best prepared by selecting a target site, preferably within about residues 114–256 and/or 362–416, inclusive, and introducing variants into the site by saturation mutagenesis.

While the site of variation is predetermined, it is unnecessary that the variation per se be predetermined. For example, in order to optimize the performance of a variation at a given site, random mutagenesis is conducted at the target codon or region and the expressed lecithin:cholesterol acyltransferase variants screened for the optimal combination of desired activity. Techniques for making substitution mutations at predetermined sites in DNA having a known sequence are well known, for example M13 primer mutagenesis.

DNA which encodes lecithin:cholesterol acyltransferase is obtained by chemical synthesis, by screening reverse transcripts of mRNA from liver, or by screening genomic libraries from any cell. In view of the length of the DNA encoding lecithin:cholesterol acyltransferase it will be more efficient to probe a cDNA library than to synthesize the DNA. However, synthesis of part of the lecithin:cholesterol acyltransferase gene is advantageous in introducing unique restriction sites at the time of preparing the DNA, thereby facilitating the use of the gene in vectors containing restriction sites otherwise not present in the native sequence, and steps can be taken to enhance translational efficiency by eliminating stem and loop structures, without the need to further modify the lecithin:cholesterol acyltransferase-encoding DNA as by mutagenesis or the like. cDNA encoding lecithin:cholesterol acyltransferase is free of introns and flanking DNA encoding other proteins homologous to the source of the lecithin:cholesterol acyltransferase DNA.

A human liver cDNA library was probed for DNA encoding human lecithin:cholesterol acyltransferase sequences using labelled oligonucleotides whose sequences were based on the partial amino acid sequence determined from analysis of purified human lecithin:cholesterol acyltransferase. The DNA encoding preLCAT or mature LCAT identified by probing then may be (FIG. 2a) mutated in order to encode the amino acid variants of lecithin:cholesterol acyltransferase described above. For example, the pre sequence is deleted and a start codon inserted immediately 5' to the DNA encoding mature lecithin:cholesterol acyltransferase so that the lecithin:cholesterol acyltransferase chain is expressed directly in recombinant culture.

Covalent labelling of this DNA is accomplished with a detectable substance such as a fluorescent group, a radioactive atom or a chemiluminescent group by methods known per se. The labelled DNA is then used in conventional hybridization assays. Such assays are employed in identifying lecithin:cholesterol acyltransferase vectors and transformants as described in the Examples infra, or for in vitro diagnosis such as detection of lecithin:cholesterol acyltransferase mRNA or aberrant genomic DNA in tissues.

A particularly valuable use of lecithin:cholesterol acyltransferase-associated DNA is to facilitate the identification of heart disease-linked restriction enzyme polymorphisms.

General methods are known for the determination of restriction enzyme polymorphisms linked to hereditary diseases such as sickle cell anemia (32,33). Lecithin:cholesterol acyltransferase-associated DNA is employed in such methods as follows. Genomic DNA or cDNA is prepared in known fashion from a population of subjects, some of whom demonstrate physiological signs of heart disease or atherosclerosis and others of whom do not. Preferably the populations are chosen from within the same family. This DNA then is digested to completion by a selected restriction enzyme and the fragments separated by electrophoresis. The DNA is transferred to nitrocellulose filters and hybridized to an lecithin:cholesterol acyltransferase-associated DNA fragment. This method generally is known as Northern hybridization (see infra). Subjects having a hereditary predisposition to atherosclerosis will show a different pattern of bands on Northern analysis than do subjects, i.e. they will show restriction digest polymorphism. For example, detection of the genetic abnormality responsible for lecithin:cholesterol acyltransferase deficiency will be a straight-forward application of restriction enzyme polymorphism now that the entire coding sequence of lecithin:cholesterol acyltransferase and its flanking genomic region have been described herein.

The restriction enzyme that produces the most reliable linkage with the atherosclerotic condition will be identified by routine screening as described above. Suitable candidates are chosen from among known restriction endonucleases (34).

The test samples preferably are λ phage libraries of lymphocyte genomic DNA, although cDNA liver libraries also are useful. The probes used in their analysis include full length lecithin:cholesterol acyltransferase cDNA, lecithin:cholesterol acyltransferase genomic DNA introns, untranslated 5' and 3' flanking regions of up to about 5000 bp, and fragments thereof. The size of the oligonucleotide probe will depend upon the target of the Northern hybridization. If the Northern is directed at determining the presence of an lecithin:cholesterol acyltransferase allele, the probe will be sufficiently small to permit detection under high stringency hybridization conditions, e.g. low temperature. For example, determination of a single nucleotide mutation will entail the use of a small probe, generally about from 10–20 bases and high stringency conditions. On the other hand, substantial deletions in the lecithin:cholesterol acyltransferase gene are detected by probes corresponding to the deletion; absence of hybridization demonstrates the presence of the undesirable allele. Generally, however, while the probe need not correspond to any particular portion of the lecithin:cholesterol acyltransferase genomic DNA, cDNA or flanking regions it is preferably a DNA which is or is complementary to about from 30 to 50 bp of the lecithin:cholesterol acyltransferase coding DNA.

Lecithin:cholesterol acyltransferase is synthesized in host cells transformed with vectors containing DNA encoding prelecithin:cholesterol acyltransferase, metmature lecithin:cholesterol acyltransferase or lecithin:cholesterol acyltransferase variants. Vectors are used to amplify the DNA which encodes lecithin:cholesterol acyltransferase, either in order to prepare quantities of DNA for further processing (cloning vectors) or for expression of lecithin:cholesterol acyltransferase (expression vectors). An expression vector is a replicable DNA construct in which a DNA sequence encoding lecithin:cholesterol acyltransferase is operably linked to suitable control sequences capable of effecting the expression of lecithin:cholesterol acyltransferase in a suitable host. Cloning vectors need not contain expression control sequences. Such control sequences include a transcriptional promoter, an optional operator sequence to control transcription, a sequence encoding suitable mRNA ribosomal binding sites (for prokaryotic expression), and sequences which control termination of transcription and translation. Expression and cloning vectors should include a selection gene to facilitate or amplify the stable expression of lecithin:cholesterol acyltransferase and/or identify transformants. However, the selection gene for maintaining lecithin:cholesterol acyltransferase expression can be supplied by a separate vector in cotransformation systems using eukaryotic host cells.

Vectors comprise plasmids, viruses (including phage), and integratable DNA fragments i.e., fragments that are integratable into the host genome by recombination. The vectors described herein for use in eukaryotic cell expression of lecithin:cholesterol acyltransferase contain plasmid sequences for cloning in microbes, where the plasmid replicates autonomously from the host genome, but the DNA is believed to integrate into the eukaryotic host cell genome upon transformation. Similarly, bacillus vectors that genomically integrate by homologous recombination in bacillus also are useful. However, all other forms of vectors which serve an equivalent function and which are, or become, known in the art are suitable for use herein.

Suitable vectors generally will contain replicon (origins of replication, for use in non-integrative vectors) and control sequences which are derived from species compatible with the intended expression host. Transformed host cells are cells which have been transformed or transfected with vectors containing lecithin:cholesterol acyltransferase-encoding DNA. Transformed host cells contain cloned DNA and, when transformed with an expression vector, also express lecithin:cholesterol acyltransferase or its derivatives. The expressed lecithin:cholesterol acyltransferase will be deposited intercellularly or secreted into either the periplasmic space or the culture supernatant, depending upon the host cell selected and the presence of suitable processing signals in the expressed protein, e.g. homologous or heterologous signal sequences.

DNA regions are operably linked when they are functionally related to each other. For example, DNA for a presequence or secretory leader is operably linked to DNA for a polypeptide if it is expressed as a preprotein which participates in the secretion of the polypeptide; a promoter is operably linked to a coding sequence if the controls the transcription of the sequence; or a ribosome binding site is operably linked to a coding sequence if it is positioned so as to permit translation. Generally, operably linked means that the DNA sequences being linked are contiguous and, in the case of secretory leaders, contiguous and in reading phase.

Suitable host cells are prokaryotes, yeast or higher eukaryotic cells. Prokaryotes include gram negative or gram positive organisms, for example *E. coli* or Bacilli. Higher eukaryotic cells include established cell lines of mammalian origin as described below. A preferred host cell is *E. coli* 294 (ATCC 31,446) although other prokaryotes such as *E. coli* B, *E. coli* X1776 (ATCC 31,537), *E. coli* W3110 (ATCC 27,325), pseudomonas species, or *Serratia Marcesans* are suitable.

Expression vectors for host cells ordinarily include an origin of replication (where extrachromosomal amplification is desired, as in cloning, the origin will be a bacterial origin), a promoter located upstream from the lecithin:cholesterol acyltransferase coding sequences, together with a ribosome binding site (the ribosome binding or Shine-Dalgarno sequence is only needed for prokaryotic expression), a polyadenylation site, and a transcriptional termination sequence. As noted, the skilled artisan will appreciate that certain of these sequences are not required for expression in certain hosts. An expression vector for use with microbes need only contain an origin of replication recognized by the intended host, a promoter which will function in the host and a phenotypic selection gene, for example a gene encoding proteins conferring antibiotic resistance or supplying an auxotrophic requirement. Lecithin:cholesterol acyltransferase DNA is typically cloned in *E. coli* using pBR322, a plasmid derived from an *E. coli* species (Bolivar, e al., 1977, "Gene" 2: 95). pBR322 contains genes for ampicillin and tetracycline resistance and thus provides easy means for identifying transformed cells.

Expression vectors, unlike cloning vectors, should contain a promoter or other transcription enhancing sequence which is recognized by the host organism. This is generally a promoter homologous to the intended host. In the case of vectors for higher eukaryotes, enhancer sequences frequently will increase transcription from promoters. Promoters most commonly used in recombinant DNA constructions include the β-lactamase (pencillinase) and lactose promoter systems (Chang et al., 1978, "Nature", 275: 615, and Goeddel et al., 1979, "Nature", 281: 544), a tryptophan (trp) promoter system (Goeddel et al., 1980, "Nucleic Acids Res." 8: 4057 and EPO Appln. Publ. No. 36,776) and the tac promoter (H. de Boer et al., 1983, "Proc. Nat'l. Acad. Sci. USA" 80: 21-25). While these are the most commonly used, other known microbial promoters are suitable. Their nucleotide sequences have been published, thereby enabling a skilled worker operably to ligate them to DNA encoding lecithin:cholesterol acyltransferase in plasmid vectors (Siebenlist et al., 1980, "Cell" 20: 269) using linkers or adaptors to supply any required restriction sites. Promoters for use in prokaryotic expression systems also will contain a Shine-Dalgarno (S.D.) sequence operably linked to the DNA encoding the lecithin:cholesterol acyltransferase, i.e. the S.D. sequence is positioned so as to facilitate translation. Generally, this means that the promoter and S.D. sequences found upstream from the second codon of a bacterial structural gene are substituted for the sequences of prelecithin:cholesterol acyltransferase located 5′ to mature lecithin:cholesterol acyltransferase. The start codon can be supplied by insertional mutagenesis or by the bacterial gene.

In addition to prokaryotes, eukaryotic microbes such as yeast cultures are transformed with lecithin:cholesterol acyltransferase-encoding vectors. *Saccharomyces cerevisiae*, or common baker's yeast, is the most commonly used among lower eukaryotic host microorganisms. However, a number of other strains are commonly available and useful herein. Yeast vectors generally will contain an origin of replication from the 2 micron yeast plasmid or an autonomously replicating sequence (ARS), a promoter, DNA encoding lecithin:cholesterol acyltransferase or its derivative, sequences for polyadenylation and transcription termination, and a selection gene. A suitable plasmid for lecithin:cholesterol acyltransferase expression in yeast is YRp7,) Stinchcomb et al. 1979, "Nature", 282: 39; Kingsman et al., 1979, "Gene", 7: 141; Tschemper et al., 1980, "Gene" 10: 157). This plasmid already contains the trp1 gene which provides a selection marker for a mutant strain of yeast lacking of ability to grow in tryptophan, for example ATCC No. 44076 or PEP4-1 (Jones, 1977, "Genetics", 85: 12). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

Suitable promoting sequences in yeast vectors include the promoters for metallothionein, 3-phosphoglycerate kinase (Hitzeman et al., 1980, "J. Biol. Chem.", 255: 2073) or other glycolytic enzymes (Hess et al., 1968, "J. Adv. Enzyme Reg.", 7: 149; and Holland et al., 1978, "Biochemistry", 17: 4900), such as enolase, glyceralidehyde-3-phosphate dehydrogenase, hexokinase, pyruvate decarboxylase, phosphofructokinase, glucose-6-phosphate isomerase, 3-phosphoglycerate mutase, pyruvate kinase, trisephosphate isomerase, phosphoglucose isomerase, and glucokinase. Suitable vectors and promoters for use in yeast expression are further descrived in R. Hitzeman et al., EP 73,657A.

Other yeast promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. In constructing suitable expression plasmids, the termination sequences associated with these genes are also ligated into the expression vector 3′ of the lecithin:cholesterol acyltransferase coding sequences to provide termination and polyadenylation of the mRNA.

Cultures of cells derived from multicellular organisms are preferred host cells herein. In principle, any higher eukaryotic cell culture is workable, whether from mammalian vertebrate or invertebrate culture. Propagation of vertebrate cells in culture per se has become a routine procedure in recent years [*Tissue Culture*, Academic Press, Kruse and Patterson, editors (1973)]. Examples of useful mammalian host cell lines are VERO and HeLa cells, Chinese hamster ovary (CHO) cell lines, and W138, BHK, COS-7 and MDCK cell lines.

The lecithin:cholesterol acyltransferase transcriptional and translation control sequences in vertebrate cell expression vectors preferably are provided from viral sources. For example, commonly used promoters are derived from polyoma, Adenovirus 2, and most preferably Simian Virus 40 (SV40). The early and late promoters of SV40 are particularly useful because both are obtained easily from the virus as a fragment which also contains the SV40 viral origin of replication (Fiers et al., 1978, "Nature", 273: 113). Smaller or larger SV40 fragments may also be used, provided the approximately 250 bp sequence extending from the Hind III site toward the Bgl I site located in the viral origin of replication is included. Further, it is also possible to utilize the lecithin:cholesterol acyltransferase genomic promoter, control and/or signal sequences normally associated with lecithin:cholesterol acyltransferase, provided such control sequences are compatible with and recognized by the host cell.

An origin of replication may be provided either by construction of the vector to include an exogenous origin, such as may be obtained from SV40 or other viral (e.g. Polyoma, Adenovirus, VSV, or BPV) source, or may be provided by the host cell chromosomal replication mechanism. If the vector is integrated into the host cell chromosome, the latter is often sufficient.

Rather than using vectors which contain viral origins of replication, mammalian cells are cotransformed with DNA encoding a selectable marker and DNA encoding lecithin:cholesterol acyltransferase or its derivative. An example of a suitable selectable marker is dihydrofolate reductase (DHFR) or thymidine kinase. Such markers are proteins, generally enzymes, that enable the identification of transformant cells, i.e., cells which had been competent to take up lecithin:cholesterol acyltransferase DNA, and the amplification of lecithin:cholesterol acyltransferase DNA. Generally, identification is by survival of transformants in culture medium that is toxic to untransformed cells of from which the cells cannot obtain a critical nutrient without having taken up the marker protein. Amplification is undertaken by culturing the identified transformants in cycles of ever-increasing selection pressure (generally, increases in the concentration of toxic component).

In selecting a preferred host mammalian cell for transfection by vectors which comprise DNA sequences encoding both lecithin:cholesterol acyltransferase and DHFR, it is appropriate to select the host according to the type of DHFR protein employed. If wild type DHFR protein is employed, it is preferable to select a host cell which is deficient in DHFR thus permitting the use of the DHFR coding sequence as a marker for successful transfection in selective medium which lacks hypoxanthine, glycine, and thymidine. An appropriate host cell in this case is the Chinese hamster (CHO) cell line deficient in DHFR activity, prepared and propagated as described by Urlaub and Chasin, 1980, "Proc. Nat'l. Acad. Sci. USA" 77: 2216.

On the other hand, if DNA encoding DHFR protein with low binding affinity for methotrexate (MTX) is used as the controlling sequence, it is not necessary to use DHFR resistant cells. Because the mutant DHFR is resistant to MTX, MTX containing media can be used as a means of selection provided that the host cells are themselves MTX sensitive. Most eukaryotic cells which are capable of absorbing MTX appear to be methotrexate sensitive. One such useful cell line is a CHO line, CHO-K1 (ATCC No. CCL 61).

Other methods, vectors and host cells suitable for adaptation to the synthesis of lecithin:cholesterol acyltransferase in recombinant vertebrate cell culture are described in M-J. Gething et al., "Nature" 293: 620-625 (1981); N. Mantei et al., "Nature" 281: 40-46; and A. Levinson et al., EP 117,060A and 117,058A.

Expression of human lecithin:cholesterol acyltransferase in a non-human recombinant host, or in eukaryotic microbes, results in human lecithin:cholesterol acyltransferase as a product by process of the recombinant cell culture which is not associated with its native glycosylation. Prokaryotic lecithin:cholesterol acyltransferase is entirely unglycosylated.

Host cells transformed with vectors as described above are cultured in nutrient media until lecithin:cholesterol acyltransferase accumulates in the culture. It may be advantageous to culture the host cell in a medium containing cholesterol or other lipids. Lecithin:cholesterol acyltransferase, like other catalytic factors that interact with lipids (23-27), contains an "interfacial" lipid-binding site and several other domains containing extended linear sequences of hydrophobic amino acids. Host cells that are acclimated or adapted to cholesterol and/or lipid metabolism, e.g. prokaryotes or eukaryotic microbes which are capable of growth on cholesterol or lipids, may be better adapted to the expression and/or secretion of lipophilic enzymes including lecithin:cholesterol acyltransferase. The lecithin:cholesterol acyltransferase will be located intracellularly when expressed directly, i.e. without a secretory leader, and one thus will assay refractile body preparations or soluble extracts of lysed cells for lecithin:cholesterol acyltransferase activity. Culture media or periplasmic fluids are recovered in known manner if the lecithin:cholesterol acyltransferase is secreted. Lecithin:cholesterol acyltransferase assays are well-known. See Example 5 infra. Lecithin:cholesterol acyltransferase is purified from the recovered extracts or media by processes known per se for the purification of lecithin:cholesterol acyltransferase from serum or plasma (see Example 1 infra).

Lecithin:cholesterol acyltransferase is administered in the form of pharmaceutically acceptable nontoxic salts, such as acid addition salts or metal complex, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. Intravenous administration in isotonic saline, phosphate buffer solutions or the like is suitable.

Lecithin:cholesterol acyltransferase should be administered under the guidance of a physician, and pharmaceutical compositions usually will contain an effective amount of the enzyme in conjunction with a conventional, pharmaceutically-acceptable carrier. The dosage will vary depending upon the specific purpose for which the lecithin:cholesterol acyltransferase is administered, usually at dosage levels sufficient to bring the patient's plasma Lecithin:cholesterol acyltransferase to at least about 25% of the lecithin:cholesterol acyltransferase activity in normal pooled plasma. Lecithin:cholesterol acyltransferase may be administered concurrently with apoproteins such as apolipoproteins A–I or D.

Lecithin:cholesterol acyltransferase desirably is administered from an implantable or skin-adhesive sustained-release article. Examples of suitable systems for lecithin:cholesterol acyltransferase include copolymers of L-glutamic acid and gamma ethyl-L-glutamate (U. Sidman et al., 1983, "Bipolymers" 22(1): 547-556), poly (2-hydroxyethyl-methacrylate) (R. Langer et al., 1981, "J. Biomed. Mater. Res." 15: 167–277 and R. Langer, 1982, "Chem. Tech." 12: 98-1-5), ethylene vinyl acetate (R. Langer et al., Id.), or poly-D-(−)-3-Hydroxybutric acid (EP 133,988A). Such articles are implanted subcutaneously or are placed into contact with the skin or mucous membranes.

With the exception of the cDNA clones describes below (which are designated "p" notwithstanding the fact that they are λ phage clones) plasmids are designated by a low case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. The various restriction enzymes used herein are commercially available and their reaction conditions, cofactors and other requirements as established by the enzyme suppliers were used. Restriction enzymes commonly are designated by abbreviations composed of a capital letter followed by other letters representing the microorganism from which each restriction enzyme originally was obtained. and then a number designating the particular enzyme. In general, about 1 μg of plasmid of DNA fragment is used with about 2 units of enzyme in about 20 μl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, [Molecular Cloning pp. 133–134).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., 1981, "Nucleic Acids Res." 9: 6103–6114, and D. Goeddel et al., 1980, "Nucleic Acids Res." 8: 4057.

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation and transfer to nitrocellulose by the method of E. Southern, 1975, "J. Mol. Biol." 98: 503–517, and hybridization as described by T. Maniatis et al., 1978, "Cell" 15, 687–701. "Northern" analysis is a hybridization method for mRNA conducted by electrophoresis of RNA in agarose gels containing a denaturing agent, such as 6% formaldehyde, followed by transfer to nitrocellulose and hybridization also as described in Maniatis et al.

"Transformation" means introducing DNA into an organism so that the DNA is replicable, either as an extrachormosomal element or chromosomal integrant. A suitable method for the transformation of E. coli is the $CaCl_2$ method of Mandel et al., 1970, "J. Mol. Biol." 53: 154.

"Ligation" refers to the process of forming phosphodiester bonds between two double stranded nucleic acid fragments (T. Maniatis et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

"Preparation" of DNA from transformants means isolating plasmid DNA from microbial culture. Unless otherwise provided, the alkaline/SDS method of Maniatis et al., Id. p. 90, may be used.

"Oligonucleotides" are short length single or double stranded polydeoxynucleotides which are chemically synthesized by known methods and then purified on polyacrylamide gels.

All literature citations are expressly incorporated by reference.

EXAMPLE 1

Purification and Sequence Analysis of Human Lecithin:cholesterol Acyltransferase Lecithin:cholesterol acyltransferase was purified from normal human plasma (500 ml) by a modification of procedures reported earlier (10). The d 1.21-1.25 g/ml fraction was isolated following preparative centrifugation of plasma in NaBr solution (1.24 g/ml). This was passed through a column (2.5×20 cm) of phenyl agarose (Pharmacia, Uppsala, Sweden) equilibrated with 3M NaCl, 1 mM EDTA, pH 7.4. After washing with 500 ml of 3M NaCl-10 mM Tris-HCl, pH 7.4, the phenyl agarose support was further washed with 0.15M NaCl-Tris buffer until the $OD_{280}$ of the eluate was <0.05. Remaining adsorbed protein was eluted with distilled water, and passed on to a column of DEAE-cellulose (DE-52, Whatman) equilibrated with 10 mM Tris-HCl, pH 7.4. The column was eluted with a gradient of NaCl (0–0.3M NaCl in 10 mM Tris-HCl, pH 7.4). The fraction containing lecithin:cholesterol acyltransferase was added to a column (1.5×4 cm) of hydroxylapatite (Biorad, hydroxylapatite HT) equilibrated with distilled water and eluted with a gradient of 0–5 mM sodium phosphate, pH 6.8 in 0.15M NaCl. The lecithin:cholesterol acyltransferase-containing fraction was collected. Any remaining apolipoprotien D (apo D) was removed if necessary, if passing these column fractions through an immunoaffinity column containing specific polyclonal antibody to apo D covalently linked to agarose by the CNBr procedure. The final product was judged to be pure by gradient gel electrophoresis as determined by silver staining.

Amino acid analysis was performed on a Beckman 6300 amino acid analyzer with ninhydrin detection. Peptides were hydrolyzed for 24 hr in constant boiling HCl at 110° C. $NH_2$-terminal sequence analysis was performed on native lecithin:cholesterol acyltransferase on a prototype gas/liquid phase sequencer with trimethylamine, phenylisothiocyanate, and trifluoroacetic acid (TFA) as reagents. Extracted anilinothiazolinone amino acid derivatives were automatically converted to phenylthiohydantoin amino acids with 25 percent aqueous TFA and were separated on a Beckman ultrasphere octyl column. Tryptic peptides were sequenced by both the gas/liquid phase sequencer or a modified Beckman model 890B sequencer. Tryptic digestion of lecithin:-cholesterol acyltransferase was performed in 0.1M Tris pH 8.0 with 0.01 percent Tween 20 at 37° C. for 18 hr with an enzyme to substrate ratio of 1:20. The digest was chromatographed on a Synchrom RP-4 column (4.6 mm × 10 cm). The elution solvents were 0.1 percent TFA in water (solvent 1) and 1-propanol containing 0.07 percent TFA (solvent 2). Peptides were eluted mRNA). Since cDNA clones may not contain the entire 5' and 3' ends of mRNAs, we followed the cDNA cloning with the isolation and DNA sequence analysis of genomic clones which overlapped the termini of the lecithin:cholesterol acyltransferase cDNA clones. This enabled us to confirm our interpretation of the lecithin:-cholesterol acyltransferase mRNA size and sequence.

Double-stranded cDNA was prepared from adult human liver RNA using reverse transcriptase in known fashion and, after S1 treatment, was ligated to synthetic oligonucleotides containing restriction sites for SalI, SstI, XhoI and an EcoRI overhanging end, as described previously (11). This DNA was inserted into the EcoRI site of λgt10 (11, 12). Nucleotide probes were prepared based on several of the amino acid sequences determined in Example 1 and end labeled with radiophosphorus. This work is summarized in Table 1 below.

TABLE 1

Peptide Sequence and Oligonucleotide Probes

Amino-terminus of LCAT-LCAT.1
Peptide sequence            Phe  Trp  Leu  Leu  Asn  Val  Leu  Phe  Pro  Pro  His  Thr  Thr  Pro
Oligonucleotide probe       TTC  TGG  CTG  CTG  AAC  GTG  CTG  TTC  CCT  CCT  CAC  ACC  ACC  CCT
Corresponding LCAT sequence TTC  TGG  CTC  CTC  AAT  GTG  CTC  TTC  CCC  CCG  CAC  ACC  ACG  CCC Tryptic Peptide - LCAT.3
Leu  Glu  Pro  Gly  Gln  Gln  Glu  Glu  Tyr  Tyr  Arg
CTG  GAA  CCT  GGC  CAG  CAG  GAG  GAG  TAC  TAC  CGG
CTG  GAG  CCC  GGC  CAG  CAG  GAG  GAG  TAC  TAC  CGC Tryptic Peptide - LCAT.4
Ile  Thr  Thr  Thr  Ser  Pro  Trp  Met  Phe  Pro  Asp  Arg
ATC  ACC  ACC  ACC  TCC  CCT  TGG  ATG  TTC  CCT  GAC  CGG
ATA  ACC  ACC  ACC  TCC  CCC  TGG  ATG  TTT  CCC  TCT  CGC
                                                  (Ser)

Tryptic Peptide - LCAT.5
Gln  Pro  Gln  Pro  Val  His  Leu  Leu  Pro  Ala  His  Gly  Ile  Gln  His  Leu  Asn  Met  Val
CAG  CCT  CAG  CCT  GTG  CAC  CTG  CTG  CCT  GCT  CAC  GGC  ATC  CAG  CAC  CTG  AAC  ATG  GTG
CAG  CCA  CAG  CCT  GTG  CAC  CTG  CTG  CCC  CTG  CAC  GGG  ATA  CAG  CAT  CTC  AAC  ATG  GTC
                                                                           (Leu)

Peptide sequence analysis (top line) led to the synthesis of the unique "long" oligonucleotide probes shown. (The actual probes were the reverse complement of these sequences so that they could be used for hybridization to RNA as well as to DNA.) The corresponding lecithin:cholesterol acyltransferase cDNA sequences are shown on the bottom line. In two cases, an amino acid coded by the cDNA differed from that prediction from peptide sequencing (as indicated by parentheses).

with a linear gradient of 1 percent solvent 1 to 50 percent solvent 2 at 25° C. with a flow rate of 1.0 ml/min using a Spectra Physics SP8000 HPLC. The efluent was monitored for absorbance at 214 and 280 nm by a Waters Associates model 440 absorbance detector.

EXAMPLE 2 cDNA Cloning

The general strategy for the isolation of full length lecithin:cholesterol acyltransferase cDNA started with the determination of limited amino acid sequence of human lecithin:cholesterol acyltransferase which was made in Example 1 (see FIG. 2a). In particular, we obtained four useful stretches of peptide sequence from the amino-terminus of the intact protein (as isolated from human plasma) and from three internal peptide fragments derived from digestion of lecithin:cholesterol acyltransferase with trypsin. Certain of these peptide sequences were used to design and synthesize a single oligonucleotide probe representing one possible codon choice for the appropriate sequence. Utilizing these DNA probes were obtained apparently full-length cDNA clones of lecithin:cholesterol. acyltransferase from a human adult liver cDNA library ("full length" is defined herein as representing the entire protein coding portion of the lecithin:cholesterol acyltransferase A λ phage library (~1.5 × 10⁶ pfu) with cDNA (>500 bp) was prepared in λgt10 as described (12,29).

About 2 million phage from the oligo(dT) primed human adult liver cDNA library in λgt10 were grown on forty 15-cm petri plates from which triplicate nitrocellulose filters were lifted. The filters were hybridized with different $^{32}$P-end labelled oligonucleotide probes in 0.75M NaCl, 75 mM trisodium citrate, 50 mM sodium phosphate (pH 6.8), 5× Denhardt's solution, 20 percent formamide, 10 percent dextran sulfate and 20 μg/ml boiled, sonicated salmon sperm DNA at 42° overnight and washed for 2 hrs in 0.15M NaCl, 15 mM trisodium citrate, 0.1 percent NaDoDSO₄ at 43°. Nineteen very strongly hybridizing duplicate positives were observed with filters hybridized with the lecithin:cholesterol acyltransferase.4 probe and with filters hybridized with both the lecithin:cholesterol acyltransferase.3 and lecithin:cholesterol acyltransferase.5 probes. Southern blots in these same hybridization solutions revealed ~10 discrete bands and Northern blots revealed a hybridizing RNA smaller than 18S. Upon rescreening with separated probes, 15 of 19 picked plaque regions rehybridized with lecithin:cholesterol acyltransferase.4, 12 also with lecithin:cholesterol acyltransferase.3 and 4 with lecithin:cholesterol acyltransferase.1, the probe based on amino-terminal protein sequence. The four phage that hybridized with the amino-terminal probe were the best candidates for full-length cDNA clones, and were subsequently plaque purified and analyzed by DNA sequencing (along with a fifth cDNA clone recovered subsequently by reprobing the libraries with DNA fragments from the original clone). Fragments were subcloned into M13 phage vectors for DNA sequencing by dideoxy chain termination (13). All sequences reported in this paper resulted from independent analysis of both DNA strands. A human genomic library in λCharon 30 (14) was screened with restriction fragments of cDNA clones by standard procedures.

EXAMPLE 3

DNA Sequence of Lecithin:cholesterol Acyltransferase cDNA

Figure 1:
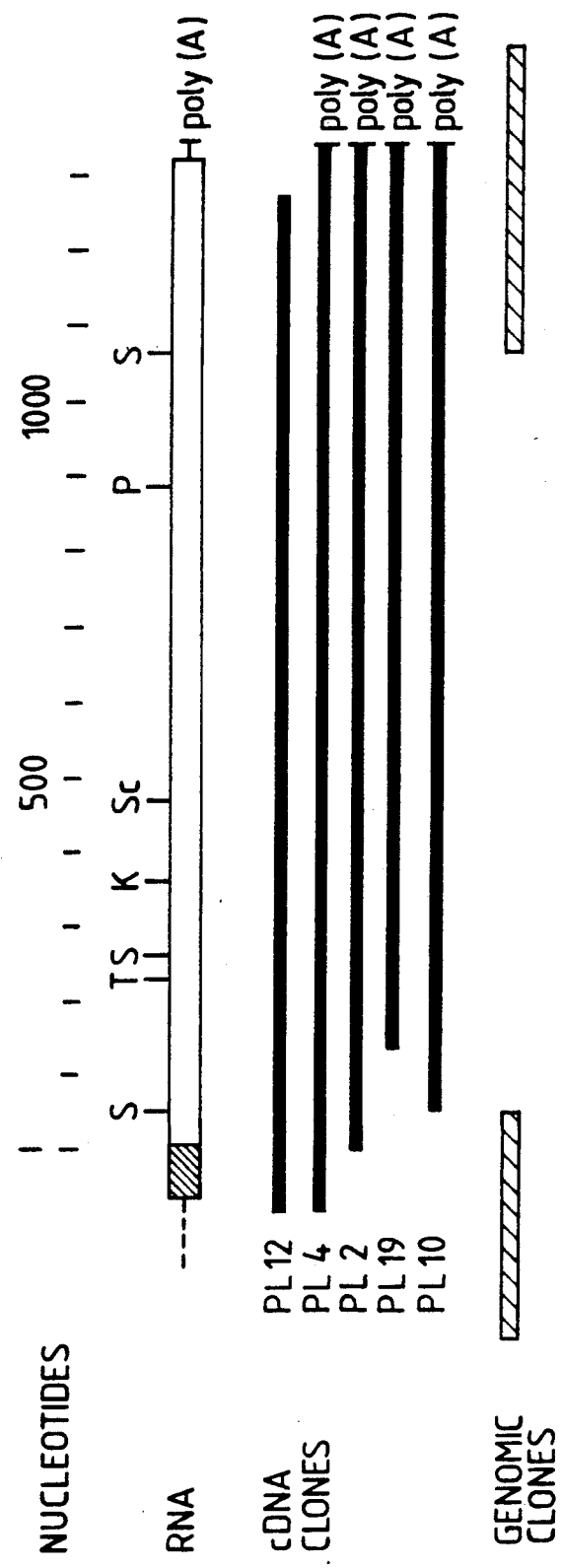
FIG. 1 depicts the human lecithin:cholesterol acyltransferase mRNA, the positions of genomic and cDNA clones, and restriction enzyme sites. Human lecithin:cholesterol acyltransferase mRNA, as deduced from the cDNA clones, is depicted below a size scale in nucleotides. The direction of transcription is from left to right. Features of the mRNA are: the 5'-untranslated region (estimated size; shown as a dotted line), the leader peptide coding region (hatched box), the mature coding region (open box), and the 3'-untranslated region ending in a polyadenylation site (line with bar). All of the sites for the restriction enzymes S (SstI), T (TagI), K (KpnI), Sc (ScaI) and P (PstI) are shown. Below this line, the five horizontal bars indicate the extent of the cDNA clones described further in the Examples. Both strands of clones pL4 and 12 were sequenced to completion, while the extent of clones pL 2, 10 and 19 were subject to C reactions only. Hatched bars on the bottom line depict regions of genomic clones which were sequenced to elucidate the terminal regions of the gene.

The extent of the five lecithin:cholesterol acyltransferase cDNA clones that were sequenced, and the deduced structure of lecithin:cholesterol acyltransferase mRNA, are shown in FIG. 1. FIG. 2 displays the DNA sequence and translated sequence of the lecithin:cholesterol acyltransferase cDNA. The DNA sequences of all five lecithin:cholesterol acyltransferase cDNA clones were similar, differing only in the extent of lecithin:cholesterol acyltransferase mRNA represented and in the length of poly(A) tails. The two longest clones, pL4 and pL12, were sequenced to completion, while C reactions only were performed for pL2, 10 and 19. Clones pL2, 4, 10 and 19 contained poly(A) tails of different lengths (50–90 b) at the same location, while pL12 did not extend back to the poly(A) tail. Clones pL4 and pL12 extended farthest at the 5' end. They both contained an initiator methionine codon and codons for an apparent hydrophobic leader sequence preceding the amino-terminal sequences of mature lecithin:cholesterol acyltransferase; the clones contained only short regions of 5'-untranslated sequence. The DNA sequence of the independent clones pL4 and pL12 were identical throughout the ~1,400 bp for which they correspond, serving to confirm the veracity of the cloning and sequencing procedures.

The 5' end of the cDNA contains an initiator methionine codon followed by a continuous open reading frame that codes for a 440 amino acid polypeptide. The first 24 residues contain a core of hydrophobic amino acids and are likely to represent an amino-terminal secretion signal peptide. Thereafter follows the sequence (beginning phe-trp-leu) of the amino terminus of the lecithin:cholesterol acyltransferase protein as it is purified from plasma. The mature protein contains 416 amino acids with a calculated molecular weight of 47,090. Lecithin:cholesterol acyltransferase is known to be a glycoprotein which migrates on SDS polyacrylamide gel at $M_r \sim 63,000$. Previous authors estimated a carbohydrate content of 25 percent and a deduced polypeptide weight of about 45,000 (2). The translated DNA sequence predicts four possible N-linked glycosylation sites (asn-X-ser; asn-X-thr). Glycosylation at one of these sites (residue 272) was detected during the course of peptide sequencing. Other potential sites of glycosylation remain unconfirmed.

The methionine codon at nucleotides 12–14 (FIG. 2a) is presumed to initiate translation of the pre-protein. This ATG is followed by G and preceded by G at minus 3 nucleotides in reasonable agreement with consensus sequences near the translation start of eukaryotic mRNA (30). None of the cDNA clones we characterized contains the entire 5' untranslated region of the message. Northern blot hybridization of human liver poly(A)+ RNA probed with lecithin:cholesterol acyltransferase cDNA clone 12 reveals a single hybridizing band of 1550±50 bases. This implies that lecithin:cholesterol acyltransferase mRNA contains approximately 100 bases of 5' untranslated sequence. Analysis of genomic clones supports this estimate, and will be described below.

The 3' end of the cDNA clone sequences reveals an unusually short 3' untranslated region of 23 nucleotides. Indeed, the common polyadenylation signal AATAAA which precedes eukaryotic poly(A) sites by 20–30 nucleotides (19) is partially contained in the codon for the carboxy terminal glutamine (GAA) and in the translation stop codon TAA. The four independent poly(A) containing clones we analyzed all had poly(A) tails at the same site. Northern blot analysis did not indicate the abundant presence of longer RNA species, suggesting that the proposed location is the major site of polyadenylation.

EXAMPLE 4

DNA Sequence of Lecithin:cholesterol Acyltransferase Genomic Clones

Due to the incomplete 5' ends and the unusual features of the 3' ends of lecithin:cholesterol acyltransferase cDNA clones, we isolated and analyzed the corresponding regions of genomic DNA. A Sau3A partial digest library of human genomic DNA in phage λCharon 30 (14) was screened with 3' and 5' terminal SstI fragments gel isolated from pL12. Five hybridizing clones were recovered and all appeared to contain the entire cDNA coding sequence as determined from restriction mapping and hybridization experiments. Phage DNA from one of these genomic clones, λL1, was cut with several restricion enzymes recognizing 5 or fewer bases, Southern blotted, and hybridized with the terminal probes. Both probes hybridized to AluI fragments ~400 bp in length. AluI-digested λL1 DNA in this size range was gel-isolated and cloned into bacteriophage M13. Plaques hybridizing to terminal SstI probes were isolated and subjected to dideoxy sequencing, resulting in the sequence of genomic fragments overlapping the 5' and 3' ends of lecithin:cholesterol acyltransferase cDNA (FIG. 2b).

The genomic sequence extends 267 bp 5' of the methionine codon presumed to initiate transcription of the pre-protein. No ATG triplets are found in this region, while stop codons occur in all three reading frames. The 3' genomic sequence extends 154 bp beyond the stop codon and agrees with the sequence of the short 3'-untranslated region and the polyadenylation site inferred from the cDNA clones. No other AATAAA sequences, nor recognized variants of this polyadenylation signal, occur in this region of the genome, which extends 134 bp beyond the poly(A) site in the cDNA clones.

EXAMPLE 5

Expression of the cloned Lecithin:cholesterol Acyltransferase Gene in COS-7 Cells The full-length lecithin:cholesterol acyltransferase cDNA was assembled from the clones pL4 and pL12 and inserted into an expression plasmid containing the SV40 origin of replication and early promoter to drive expression of lecithin:cholesterol acyltransferase coding sequences. cDNA clone pL12 was digested with EcoRI plus PstI and a ~1000 bp fragment containing the 5' part of lecithin:cholesterol acyltransferase cDNA was gel isolated. Likewise a ~500 bp EcoRI/PstI fragment of pL4 was isolated, which contains the 3' part of the cDNA. These two fragments were ligated into the EcoRI site of pUC8 (New England Bio Labs) thus fusing the entire lecithin:cholesterol acyltransferase coding region at its internal PstI site. This intermediate recombinant plasmid was digested with EcoRI and the approximately 1500 bp lecithin:cholesterol acyltransferase cDNA fragment was isolated.

The plasmid pgDtruncDHFR(16) contains an SV40 origin of replication and early promoter directing the synthesis the herpes simplex virus gD protein from cDNA encoding the gD protein. The starting plasmid also contains a second SV40 promoter driving expression of a DHFR gene, as well as pML (35) sequences for replication and drug selection in *E. coli*. Hence it serves as a shuttle vector capable of growth in *E. coli* as well as mammalian tissue culture cells. pgDtruncDHFR was digested with EcoRI and the vector fragment isolated. The vector fragment then was ligated to the 1500 bp fragment isolated alone, and the ligation mixture used to transform *E. coli* 294 (ATCC 31,446) cells.

Ampicillin resistant plasmids were selected and probed for the lecithin:cholesterol acyltransferase gene. One positively hybridizing colony was recovered and designated pSVLCAT.1. This plasmid is shown in FIG. 3. COS7 (monkey kidney) cells at a density of $1.5 \times 10^6$ cells per 60 mm dish were rinsed in serum-free Minimum Eagle's Medium, transfected with plasmid pSVLCAT (4 $\mu$g/ml) and DEAE (200 $\mu$g/ml) (17) in the same medium for 5 hrs at 37° C. and 7 percent $CO_2$, rinsed in serum-free growth medium and grown in 2.5 ml serum-free growth medium for 60 hrs. (Serum-free growth medium is medium F-12 supplemented with 5 mg/ml insulin and 10 mg/ml transferrin.) Supernatants were removed and assayed immediately. The efficiency of transfection under these conditions was 20 percent, using cotransformation with a plasmid containing the herpes gD surface protein and an immunofluorescence assay for the gD protein. Control cultures of COS7 cells were subjected to the same transfection and growth protocol, except that pSVLCAT.1 DNA was not included. No attempt was made at this time to amplify or select lecithin:cholesterol acyltransferase expression by methotrexate selection, although this is preferable for maximum levels of lecithin:cholesterol acyltransferase expression.

Culture supernatants were assayed for lecithin:cholesterol acyltransferase activity as previously described (10). In brief, single-walled vesicles were prepared by French pressing from a suspension of egg lecithin, freshly repurified 1,2-$^3$H-cholesterol (New England Nuclear) and free cholesterol (weight ratio 8/1) in distilled water. Cholesterol specific activity was $1.2 \times 10^5$ dpm/$\mu$g. Vesicles (100 $\mu$g cholesterol/ml) were incubated with apo A-I (100 $\mu$g/ml) for 60 min at 37° C. The activated vesicles were mixed with an equal volume of 10 percent w/v recrystallized human albumin in 0.15M NaCl, 10 mM Tris-HCl, pH 7.4. Portions of culture medium were added in a total assay vol of 0.4 ml, and the mixture incubated (60 min) at 37° C. The reaction was stopped by addition of an equal volume of methanol, then labeled cholesteryl esters were extracted with chloroform. Portions of the chloroform phase were fractionated on silica gel layers developed in hexane-diethyl ether-acetic acid 83/16/1 v/v/v. Cholesteryl ester radioactivity was determined by liquid scintillation spectrometry. Activity is expressed as picomoles of cholesterol ester synthesized per ml of culture medium per hour.

In three separate experiments, lecithin:cholesterol acyltransferase in the activity in the medium of transfected cells averaged $4 \pm 1.9$ pmoles $ml^{-1} h^{-1}$ (three transfections: 6.5, 1.9 and 3.6 pmoles $ml^{-1} h^{-1}$, cell density was somewhat low in the second experiment), while activity in the medium of control cells cultured under the same conditions was $0.5 \pm 0.4$ pmoles $ml^{-1} h^{-1}$. There are no detectable activity in the medium when 1.5 mM DTNB, a known lecithin:cholesterol acyltransferase inhibitor (31), was included in the assay medium, or when apo A-I was not present. These data indicate that the appearance of lecithin:cholesterol acyltransferase in the culture medium is induced after transfection with plasmid pSVLCAT.1, and that this activity has the properties of the plasma enzyme in terms of its cofactor dependence, and inhibition by sulfhydryl reagents. This verifies that the cloned cDNA encodes lecithin:cholesterol acyltransferase, which is expressed in heterologous cells as a recombinant DNA derived product.

Bibliography

1. Fielding, C. J. and Fielding, P. E. (1980) Med. Clinics N. Am. 66, 363-373.
2. Chung, J., Abano, D. A., Fless, G. M., and Scanu, A. M. (1979) J. Biol. Chem. 254, 7456-7464.
3. Doi, Y. and Nishida, T. (1983) J. Biol. Chem. 258, 5840-5846.
4. Osuga, T. and Portman, O. W. (1970) Am. J. Physiol. 220, 735-741.
5. de Parscau, L. and Fielding, P. E. (1984) J. Lip. Res. 25, 721-728.
6. Fielding, C. J., Shore, V. G. and Fielding, P. E. (1972) Biochem. Biophys. Res. Comm. 46, 1493-1498.
7. Fielding, C. J. and Fielding, P. E. (1981) Proc. Natl. Acad. Sci. USA 78, 3911-3914.
8. Davis, R. A. Halgerud, P., Dueland, S., and Drevon, C. A. (1982) Biochem. Biophys. Acta. 689, 410-414.
9. Glomset, J. A. and Norum, K. R. (1973) Adv. Lipid Res. 11, 1-65.
10. Aron, L., Jones, S., and Fielding, C. J. (1978) J. Biol. Chem. 253, 7220-7226.
11. Ullrich, A. et al. (1984) Nature 309, 418-425.
12. Huynh, T., Young, R., and Davis, R. in Practical Approaches in Biochemistry (ed. Grover, D.) (IRL, Oxford, 1984).
13. Messing, J., Crea, R., and Seeburg, P. H. (1981) Nucl. Acids Res. 9, 309-321.
14. Wood, W. I. et al. (1984) Nature 312, 330-337.
15. Denhardt, O. (1966) Biochem. Biophys. Res. Commun. 23, 641-646.
16. Lasky, L. A. et al. (1984) Biotechnology 2, 527-532.
17. McCutchan, J. H. and Pagano, J. (1968) J. Natl. Cancer Inst. 41, 351-357.
18. Chong, K. S., Jahani, M., Hara, S., and Lacko, A. G. (1983) Can. J. Biochem. Cell Biol. 61, 875-881.
19. Proudfoot, N. and Brownlee, G. (1981) Nature 252, 359-362.
20. Anderson, S. and Kingston, I. B. (1983) Proc. Natl. Acad. Sci. USA 80, 6836-6842.

21. Ullrich, A. et al. (1984) EMBO J. 3, 361-364.
22. Doi, Y. and Nishida, T. (1981) Fed. Proc. 40, 1695.
23. Pujik, W. C., Verhij, H. M. and de Haas, G. H. (1977) Biochem. Biophys. Acta 492, 254-259.
24. de Caro, J. et al. (1981) Biochem. Biophys. Acta. 671, 129-138.
25. Akeryod, R. et al. (1981) Eur. J. Biochem. 114, 385-391.
26. Rouard, M. et al. (1978) Biochem. Biophys. Acta. 530, 227-235.
27. Docherty, A. J. P. et al. (1985) Nucleic Acids Res. 13, 1891-1903.
28. Albero et al., (1981) J. Cancer Inst. 67, 141-148.
29. Ullrich, A., et al. (1984) Nature 309, 418-425.
30. Kozak, M. (1980) Nucl. Acids Res. 8, 127-142.
31. Stokke, K. T. et al. (1971) Scand. J. Clin. Lab. Invest. 27, 21-27.
32. Kan, Y. et al. (1978) Proc. Natl. Acad. Sci. USA 75, 5631-5635.
33. Botstein et al. (1980) Am. J. Hum. Genet. 32, 314.
34. Maniatis et al. (1982) Molecular Cloning pp. 100-101.
35. Lusky et al. (1981) Nature 293, 79.

We claim:

1. A method for detecting a human lecithin:cholesterol acyltransferase gene or parts thereof comprising digesting a test sample of DNA with a restriction enzyme to produce a population of DNA fragments, separating the fragments and determining those fragments of at least 10 nucleotides capable of hybridizing under high stringency conditions to a human lecithin:cholesterol acyltransferase nucleic acid probe which is complementary to human lecithin:cholesterol acyltransferase DNA selected from the group consisting of human lecithin:cholesterol acyltransferase encoding structural genomic DNA, cDNA, the flanking regions of FIG. 2, or a portion of a human lecithin:cholesterol acyltransferase structural gene which will hybridize specifically to a human lecithin:cholesterol acyltransferase structural gene.

2. The method of claim 1 wherein the nucleic acid probe is both complementary to a portion of the lecithin:cholesterol acyltransferase structural genomic DNA and will specifically hybridize to a human lecithin:cholesterol acyltransferase structural gene.

3. The method of claim 1 wherein the probe is about from 10 to 50 nucleotides in length.

4. A predetermined labelled fragment of at least 10 nucleotides of a human lecithin:cholesterol acyltransferase nucleic acid which fragment is both complementary to and will specifically hybridize to a human lecithin:cholesterol acyltransferase DNA selected from the group consisting of a human lecithin:cholesterol acyltransferase encoding genomic DNA, cDNA, the flanking regions of FIG. 2, or a portion of the human lecithin:cholesterol acyltransferase structural gene which will hybridize specifically to the human lecithin:cholesterol acyltransferase structural gene.

* * * * *